US012502306B2

(12) United States Patent
Berria

(10) Patent No.: US 12,502,306 B2
(45) Date of Patent: Dec. 23, 2025

(54) REVERSIBLE MALE CONTRACEPTIVE IMPLANT DEVICE

(71) Applicant: Mikel Hilario Berria, Las Vegas, NV (US)

(72) Inventor: Mikel Hilario Berria, Las Vegas, NV (US)

( * ) Notice: Subject to any disclaimer, the term of this patent is extended or adjusted under 35 U.S.C. 154(b) by 0 days.

(21) Appl. No.: 18/418,300

(22) Filed: Jan. 21, 2024

(65) Prior Publication Data

US 2024/0415694 A1 Dec. 19, 2024

Related U.S. Application Data

(60) Provisional application No. 63/521,135, filed on Jun. 15, 2023.

(51) Int. Cl.
*A61F 6/24* (2006.01)

(52) U.S. Cl.
CPC .................................... *A61F 6/24* (2013.01)

(58) Field of Classification Search
CPC .... A61F 6/24; A61F 6/20; A61F 6/065; A61F 6/005; A61F 6/06; A61F 6/225; A61F 6/22; A61F 6/02; A61M 25/1011; A61M 2025/1052; A61M 2210/16; A61M 25/10; A61B 17/12131; A61B 17/12136; A61B 17/12022
See application file for complete search history.

(56) References Cited

U.S. PATENT DOCUMENTS

2014/0048076 A1* 2/2014 Hollander ................ A61F 6/20 128/843

* cited by examiner

*Primary Examiner* — Ophelia A Hawthorne
(74) *Attorney, Agent, or Firm* — Malloy & Malloy, PL; Rafay Asrar

(57) ABSTRACT

The present invention introduces a groundbreaking solution in the field of male contraception-a reversible male birth control implant device. The device offers enhanced flexibility in family planning by controlling the amount of sperm ejaculated. It consists of a tubular component surgically inserted into each severed vas deferens, with a wireless receiver attached. The wireless receiver receives external wireless signals and enables the device to switch between a state that permits the flow of sperm and a state that impedes it. The device also features an outlet for the safe elimination of obstructed sperm. The use of biocompatible materials and compatibility with medical imaging devices, such as MRI, ensures safety and usability. This innovative device empowers individuals with convenient and discreet control over their fertility, revolutionizing male contraception and opening new possibilities in reproductive health.

20 Claims, 8 Drawing Sheets

REVERSIBLE MALE CONTRACEPTIVE IMPLANT DEVICE

FIELD OF THE INVENTION

The present invention relates generally to the field of male contraception, and more specifically, to a reversible male birth control implant device that provides enhanced control and flexibility in family planning. The device incorporates a design with a wireless receiver attached that enables controlled blocking and unblocking of sperm flow, thereby regulating the amount of sperm ejaculated.

BACKGROUND OF THE INVENTION

The critical role of birth control and family planning in global health, societal growth, and individual wellness is universally recognized. Despite this recognition, the field of male contraception continues to grapple with numerous challenges, characterized by limitations in efficacy, convenience, reversibility, and the range of options available.

In this background section, we highlight these limitations by reviewing traditional male contraception methods, namely condoms, withdrawal, and vasectomy. We also consider the more recent chemical and hormonal approaches to male contraception, which, despite promising advancements, continue to present significant challenges.

Condoms, widely known as the primary non-permanent method of male contraception, present a variety of issues, chiefly user compliance and a higher than desirable failure rate. Improper usage, breakage, and slippage often contribute to this failure rate. Condoms also have the potential to cause discomfort and diminish sexual pleasure for some men, which can further hinder user compliance.

The withdrawal method, or coitus *interruptus*, is fraught with unreliability. As it requires excellent timing and self-control, the failure rate is high. Further, it offers no protection against sexually transmitted infections, making it a less desirable choice for many.

Vasectomy, a surgical procedure involving the cutting, blocking, or sealing of the vas deferens, is a more effective option, but it carries its own set of drawbacks. Primarily, it is seen as a permanent solution, with reversal being complex, expensive, and often not fully successful. This permanence is a significant deterrent for many men, particularly younger individuals who may wish to have children in the future.

The development of chemical and hormonal methods of contraception for men has been a burgeoning field of research. However, despite ongoing efforts, these methods have not yet achieved widespread commercial use. Potential side effects associated with these methods are a significant concern. These can include hormonal imbalances, mood swings, and long-term health risks. Furthermore, the efficacy and reversibility of these methods are still areas of uncertainty, requiring more research and development to confirm their suitability and safety.

The issues enumerated above underscore the significant deficiencies in the field of male contraception. The available options are often associated with low reliability, high failure rates, discomfort, permanent or semi-permanent effects, and potential health risks. The lack of a male contraceptive method that is reliable, convenient, fully reversible, and free from adverse side effects presents a considerable gap in the field.

Furthermore, the social and psychological implications of these limitations cannot be ignored. The burden of birth control often falls disproportionately on women due to the lack of effective and convenient male contraception options. This imbalance can contribute to various societal issues, including gender inequality in reproductive health and the high costs and potential health risks of female contraception.

In the light of these challenges, the field of male contraception stands at a pivotal juncture. There is a clear and pressing need for a novel approach that offers enhanced efficacy, convenience, and reversibility, and that addresses the limitations inherent in existing methods. Such an approach could radically redefine the landscape of male contraception, providing men with greater control and flexibility in family planning and helping to address some of the longstanding issues in reproductive health. The invention of such a solution would indeed represent a monumental advancement in the field, opening up new horizons in contraceptive technology and reproductive health.

SUMMARY OF THE INVENTION

The present invention pertains to a novel reversible male birth control implant device, designed to provide enhanced flexibility in family planning. This device features a small tube, fabricated from a biocompatible material compatible with medical imaging devices, which is surgically inserted into each severed vas deferens. The device incorporates a wireless receiver capable of receiving external signals, thus enabling the device to switch between a state permitting the flow of sperm and a state blocking the flow of sperm. When in the closed state, an outlet in the device allows the sperm to exit into the scrotum, where it is naturally phagocytized by the body's immune system.

The invention offers several significant advantages over conventional male contraception methods. Unlike methods such as condoms and withdrawal, the device provides a highly reliable, non-permanent contraceptive solution with a low risk of user error. Contrary to vasectomy, this device is fully reversible and does not require complex surgical procedures for reversal, thus providing more flexibility for users who may wish to have children in the future. Unlike experimental chemical and hormonal methods, the device does not induce hormonal imbalances or other potential side effects, making it a safer option. Additionally, the wireless control feature provides a non-invasive method of toggling between the device's contraceptive and non-contraceptive states, enhancing the convenience and user-friendliness of this solution. Overall, this invention addresses several limitations of existing male contraception methods, representing a significant advancement in the field of family planning and reproductive health.

In a first implementation of the invention, a reversible male contraceptive implant device comprises:

- a tubular component configured for surgical insertion into each severed vas deferens, wherein the proximal and distal ends of each vas deferens are attachable to respective ends of the tubular component;
- a wireless receiver coupled to the tubular component, capable of receiving external wireless signals, and responsive to said signals by alternating the device between a first state that permits the flow of sperm through the tubular component and a second state that impedes the flow of sperm;
- an outlet configured to allow sperm to exit the tubular component into the scrotum when the device is in the second state; and a mechanism for directly switching between the first state and the second state, wherein said mechanism is actuated by the wireless receiver in response to the received wireless signals.

In a second aspect, the tubular component may be constructed from a flexible, resilient, biocompatible material compatible with medical imaging devices.

In another aspect, the tubular component may be constructed from Polytetrafluoroethylene (Teflon®).

In another aspect, the wireless receiver does not contain any metals incompatible with MRI imaging tools.

In another aspect, the wireless receiver may be configured to receive two or more specific wireless signals to switch between the first and second states for security and safety purposes.

In another aspect, the wireless receiver can receive one or a combination of non-biologically harmful wave signals such as radio frequency, ultrasound, and infrared light.

In another aspect, the wireless receiver may convert the received wireless signals directly into electrical and then mechanical energy without the need for an internal battery.

In another aspect, the mechanism for directly switching between the first and second states works with a semi-flexible tube.

In another aspect, the semi-flexible tube may be dilatated in the middle, and uses a diaphragm in the dilatated portion that can be pulled taut to the smaller proximal lumen of the device in order to impede the flow of sperm.

In another aspect, the mechanism for switching between states of sperm flow and obstruction may involve inflation and deflation of an internal balloon.

In another aspect, the mechanism for switching between states of sperm flow and obstruction may involve a ball valve.

In another aspect, the internal balloon or ball valve are made from a biocompatible material that minimizes the risk of damage to the sperm during the transition between states.

In another aspect, the mechanism to switch between the first and second states may be powered by a small copper coil in the device that can receive wireless power transmission.

In another aspect, the tubular component may be dilated in the middle portion and the mechanism for switching between the first and second states involves a diaphragm, wherein said diaphragm is made of silicon, Teflon®, or another safe material.

In another aspect, the wireless receiver may require a unique sequence of wireless signals to transition between the first and second states, enhancing the security of the device operation.

In another aspect, the wireless receiver may be shielded to prevent accidental actuation from environmental wireless signals.

In another aspect, the outlet allowing sperm to exit into the scrotum may be biocompatible and designed to minimize any immunological response.

In another aspect, the diaphragm used in the dilatated portion of the semi-flexible tube may be designed and configured to return to its original shape after each transition between the first and second states, ensuring a prolonged lifespan of the device.

In another aspect, the device may be designed and configured to facilitate easy surgical insertion and removal, thus providing a user-friendly, non-permanent solution for male contraception.

In another aspect, the wireless receiver may be configured to provide a confirmation signal back to the user upon successful transition between the first and second states, ensuring reliable operation.

In another implementation of the invention, a method of providing reversible male contraception comprises:

surgically implanting a device with a tubular structure in each severed vas deferens such that the proximal and distal ends of each vas deferens are attached to the respective ends of the tubular structure of the device;

operating a wireless receiver attached to the device to receive external wireless signals, which in response, switches the device between a first state that permits the flow of sperm through the tubular structure and a second state that inhibits the flow of sperm;

managing the exit of sperm from the tubular structure into the scrotum through an outlet within the device when the device is in the second state; and employing a mechanism within the device, which is actuated by the wireless receiver upon receiving the signals, to facilitate a direct transition between the first and second states.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present detailed description provides an in-depth analysis of a groundbreaking invention in the field of male contraception-a reversible male birth control implant device 100. This device 100 aims to control the amount of sperm ejaculated, thereby offering enhanced flexibility in family planning and revolutionizing the realm of reproductive health.

Figure 1:
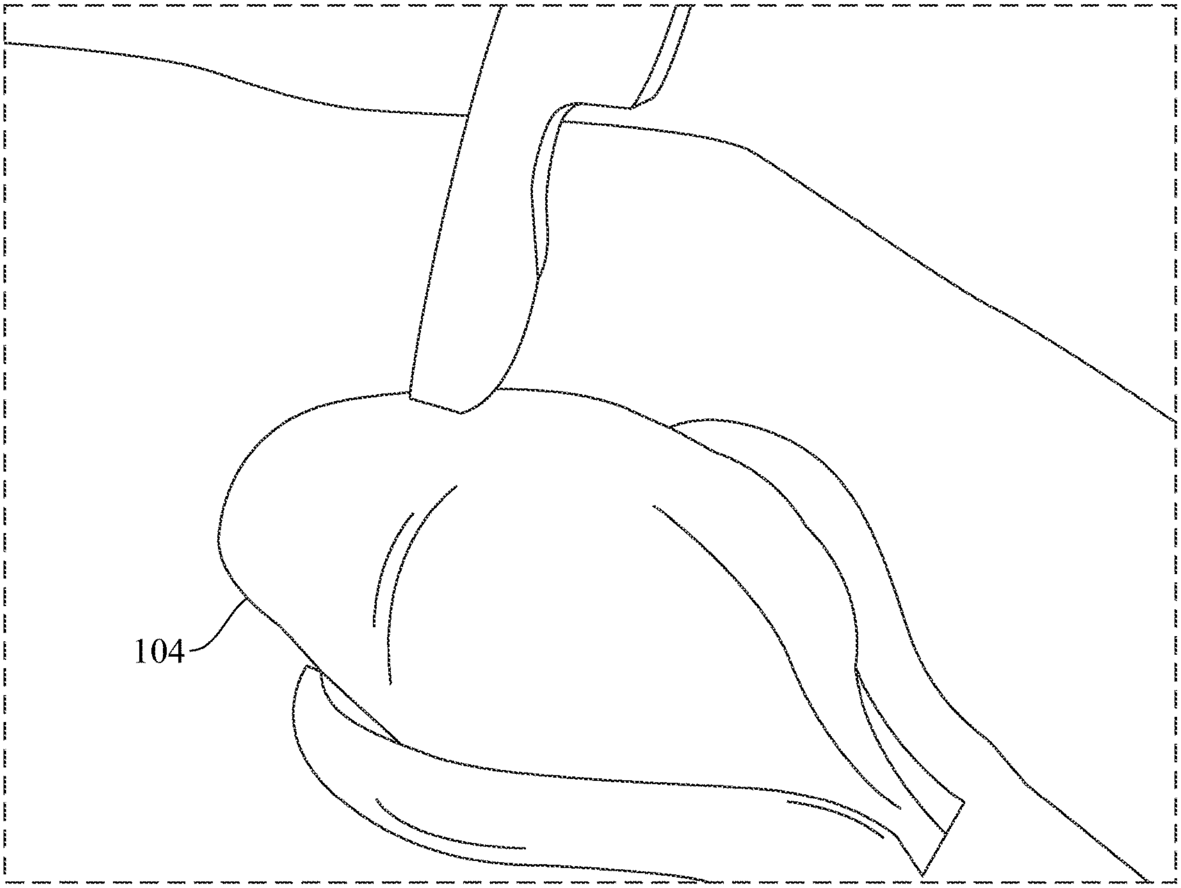
FIG. 1 presents a front perspective view of a scrotum being prepared for surgical implantation of the present invention.

The surgical procedure begins with the preparation of the scrotum 104, ensuring a sterile environment for the operation (FIG. 1). Sterilization techniques, including thorough cleansing with antiseptic solutions, are employed to minimize the risk of infection and create an optimal surgical field. This meticulous preparation ensures the highest standards of hygiene and safety for the patient.

Figure 2:
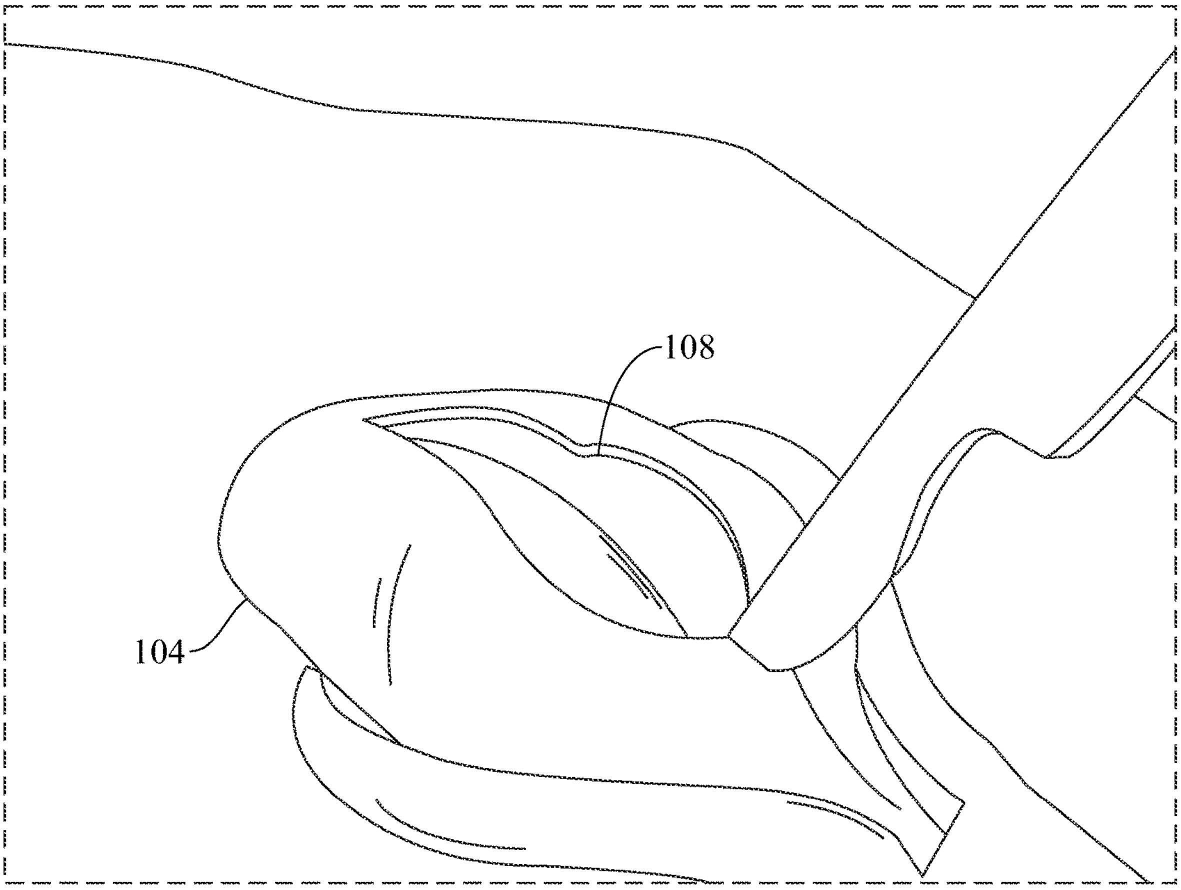
FIG. 2 presents a front perspective view of the scrotum illustrated in FIG. 1, shown after the scrotum has been cut open.

Following the scrotal preparation, a precise incision 108 is made in the scrotum (FIG. 2). The incision 108 is performed with surgical precision to minimize tissue damage and promote optimal healing. Great care is taken to create a clean and well-controlled surgical site, providing an ideal environment for the subsequent steps of the procedure.

Figure 3:
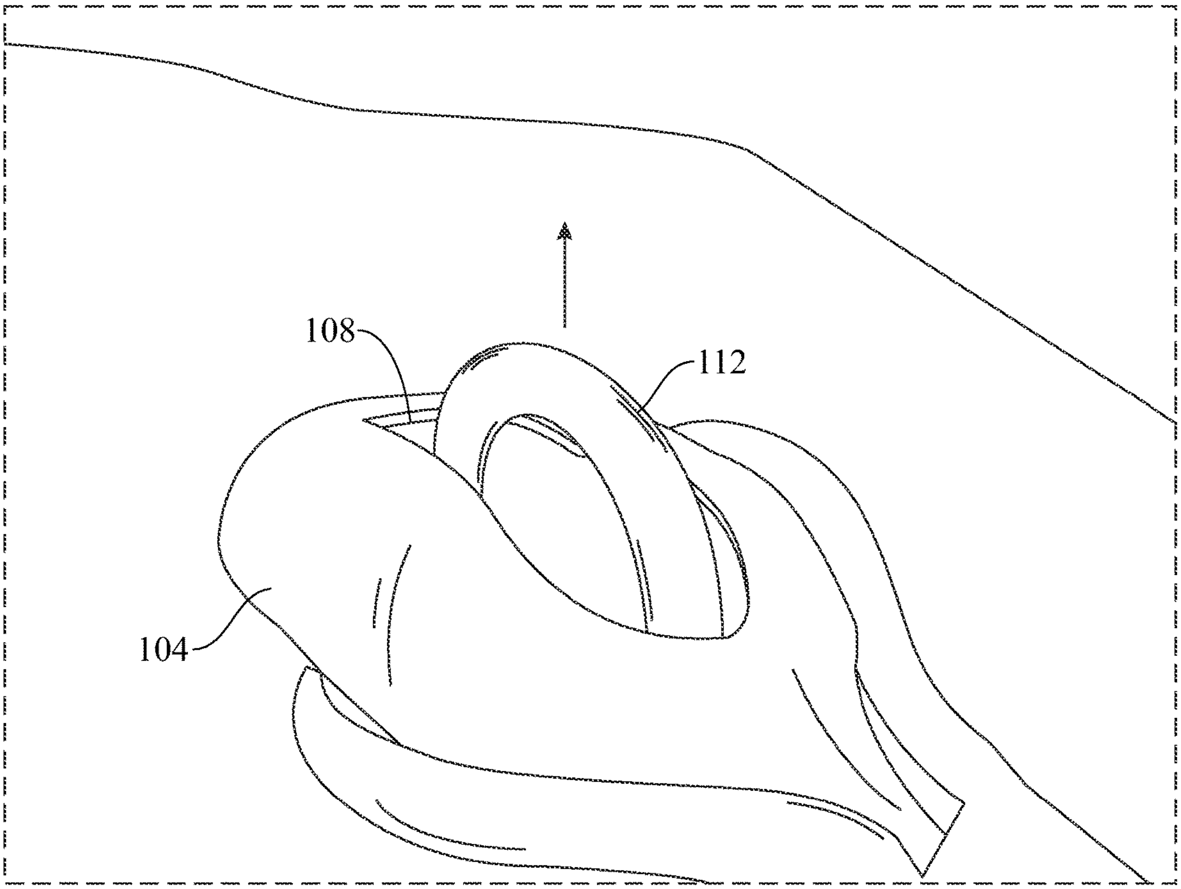
FIG. 3 presents a front perspective view of the scrotum illustrated in FIG. 2, shown after the scrotum has been cut open and a vans deferens has been pulled out.

After the incision, the vas deferens 112, which is the primary conduit for sperm transportation from the testicles to the urethra, is carefully pulled out from the scrotum (FIG. 3). Delicate techniques are employed to isolate the vas deferens, ensuring minimal trauma to the surrounding tissues.

Figure 4:
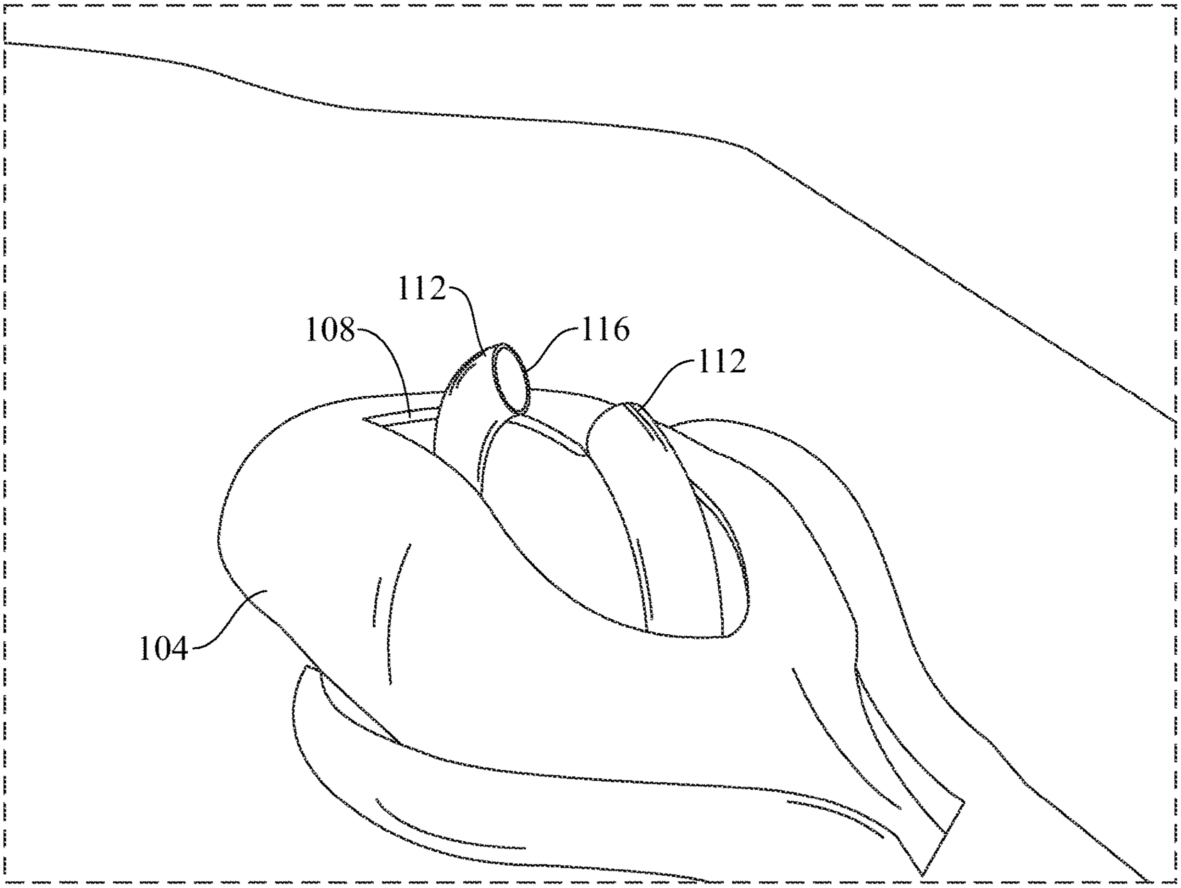
FIG. 4 presents a front perspective view of the scrotum illustrated in FIG. 3, shown after the scrotum has been cut open, a vans deferens has been pulled out, and a cut has been made into the vans deferens.

With the vas deferens exposed, a precise incision 116 is made to create an opening (FIG. 4). This incision is critical for the attachment of the reversible male birth control implant device and is executed with surgical precision to ensure proper alignment and minimize the risk of sperm leakage.

Figure 5:
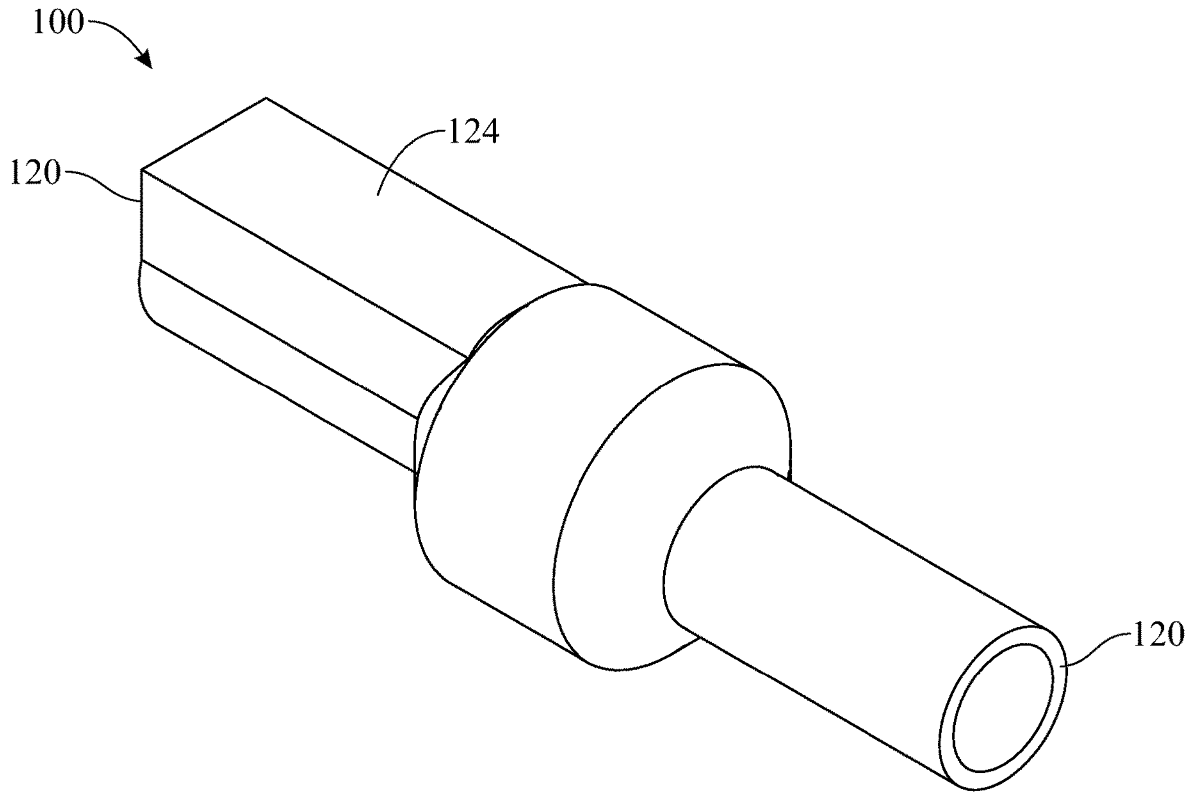
FIG. 5 presents a front perspective view of the reversible male contraceptive implant device, in accordance with a first illustrative embodiment of the invention.

Now turning our attention to FIG. 5, we observe the reversible male contraceptive implant device 100 itself. This device 100 comprises a tubular component 120 designed for surgical insertion into each severed vas deferens. The proximal and distal ends of each vas deferens 112 are attachable to respective ends of the tubular component 120. The tubular component 120 is constructed from a flexible, resilient, and biocompatible material that ensures compatibility with the human body. Polytetrafluoroethylene (Teflon®), a well-established material used in vascular surgeries, is identified as a suitable candidate due to its biocompatibility and compatibility with medical imaging devices, including MRI. The use of Teflon® in the construction of the tubular component enhances the safety and effectiveness of the device.

Figure 6:
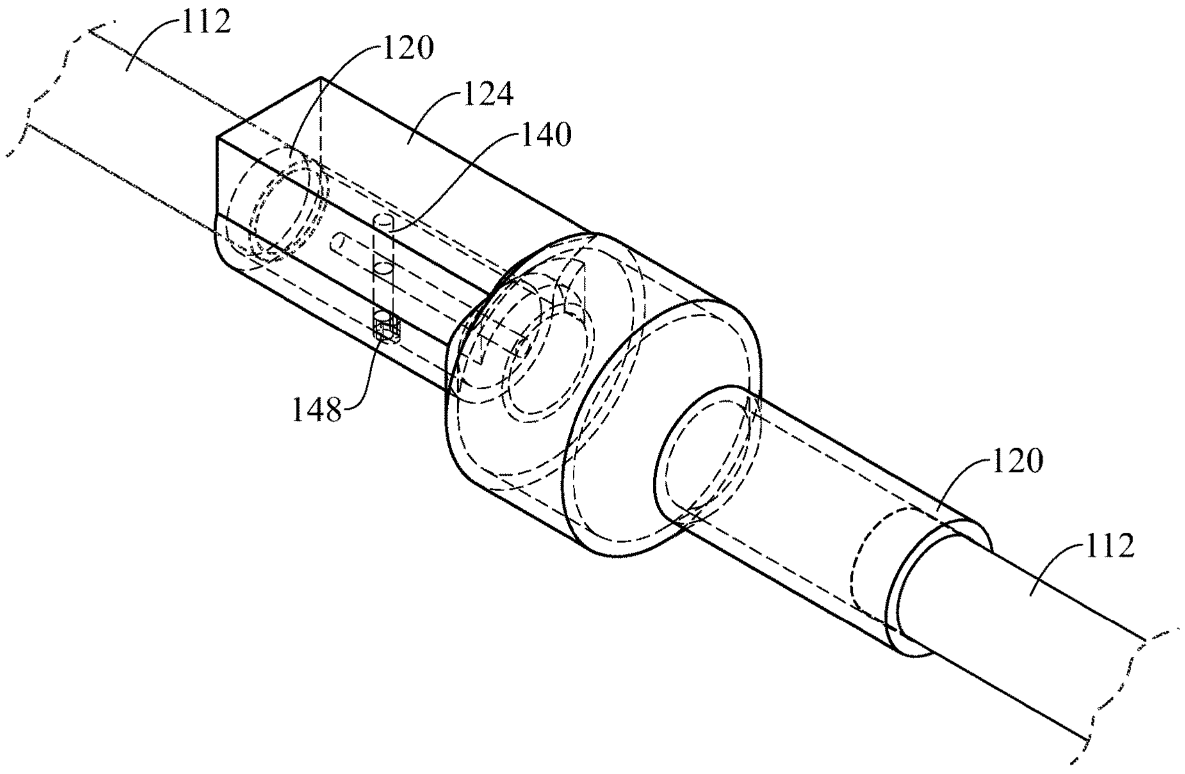
FIG. 6 presents a front perspective, transparent view of the reversible male contraceptive implant device illustrated in FIG. 5, shown attached to the vans deferens from FIGS. 2-4.

Attached to the tubular component is a wireless receiver 124, as illustrated in FIG. 6. The wireless receiver is designed to receive wireless signals 128 (FIG. 8) from an external controller. It is capable of wirelessly switching the device between a first state (FIG. 7) that permits the flow of sperm 132 through the tubular component 120 and a second state (FIG. 8) that impedes the flow of sperm 132. The wireless receiver is shielded to prevent accidental actuation from environmental wireless signals. It is also designed to be compatible with medical imaging tools, such as MRI, without containing any metals that may interfere with the imaging process.

The wireless receiver 124 is responsive to the signals received, allowing for a direct switch between the first state and the second state of the device. The wireless receiver 124 requires two or more specific wireless signals 128 to switch between the states of allowing or blocking the flow of sperm 132, enhancing the security and safety of the device operation. The wireless signals 128 used for switching can include radio frequency, ultrasound, and infrared light, among others. The wireless receiver converts these wireless signals 128 directly into electrical and mechanical energy, eliminating the need for an internal battery. Additionally, embodiments are envisioned wherein the wireless receiver 124 may emit wireless signal 128 to a smartphone to serve as a "sexual partner proof" of the user being sterile or not depending on the state of the device 100.

Figure 7:
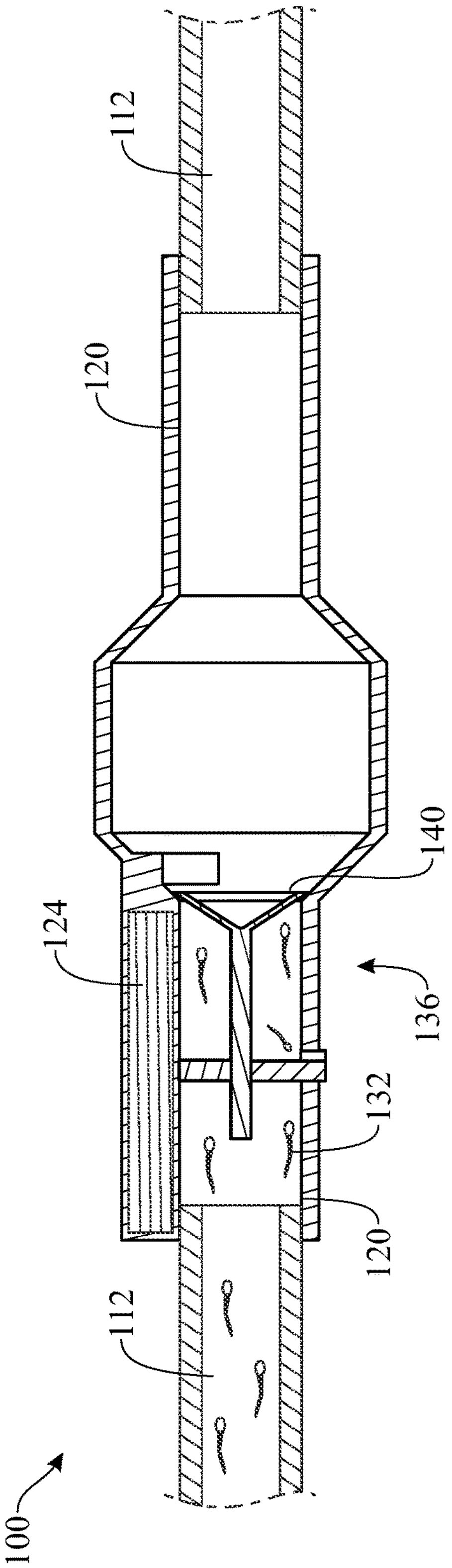
FIG. 7 shows a side, longitudinal cross-sectional view of the reversible male contraceptive implant device illustrated in FIG. 5, shown in a state of sperm obstruction.

FIG. 7 provides a side, longitudinal cross-sectional view of the device 100 in a state of sperm obstruction 136. This state is achieved through the device's switching mechanism, which includes a diaphragm 140 made of silicon, Teflon®, or another suitable material within a dilatated portion of the tubular structure. The diaphragm 140 can be pulled towards the smaller proximal lumen of the device, effectively impeding the flow of sperm 132. This switching mechanism ensures a reliable transition between the states of allowing or blocking the flow of sperm 132.

Figure 8:
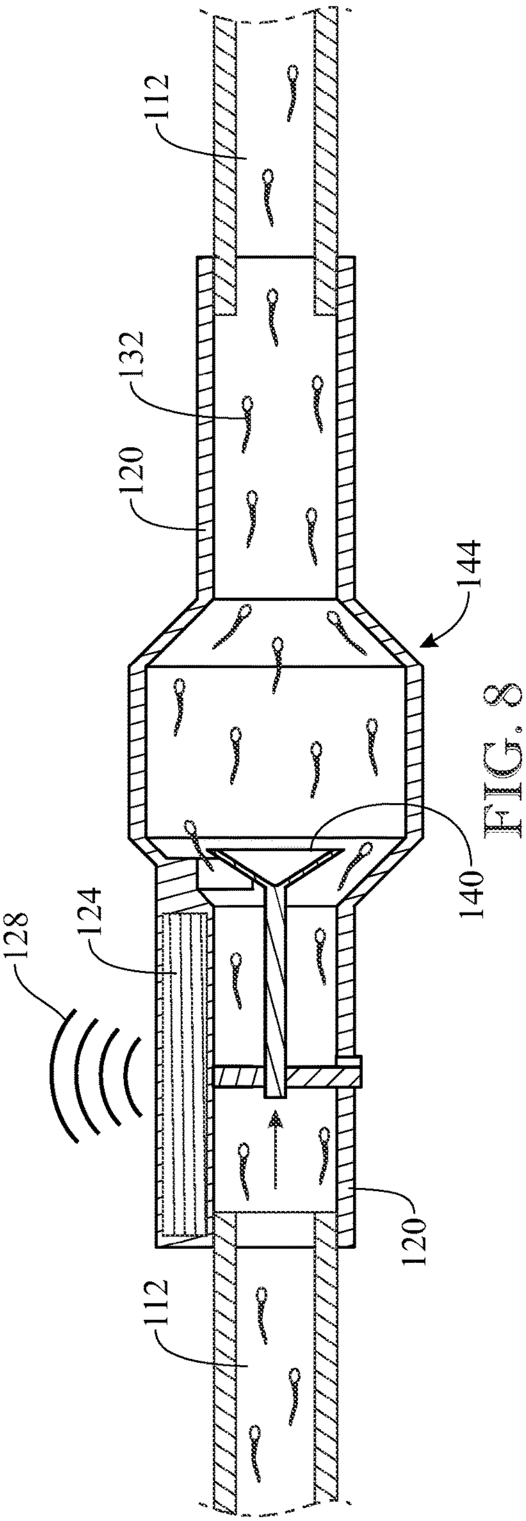
FIG. 8 shows a side, longitudinal cross-sectional view of the reversible male contraceptive implant device illustrated in FIG. 5, shown in a state of sperm flow.

Conversely, in FIG. 8, we witness the device in a state of sperm flow 144. In this state, the diaphragm 140 is repositioned to clear the lumen, allowing for the unobstructed movement of sperm through the tubular component 120. The wireless receiver 124, in response to the signals 128 received, actuates the switching mechanism to transition the device between the states of allowing and blocking sperm flow 132.

Figure 9:
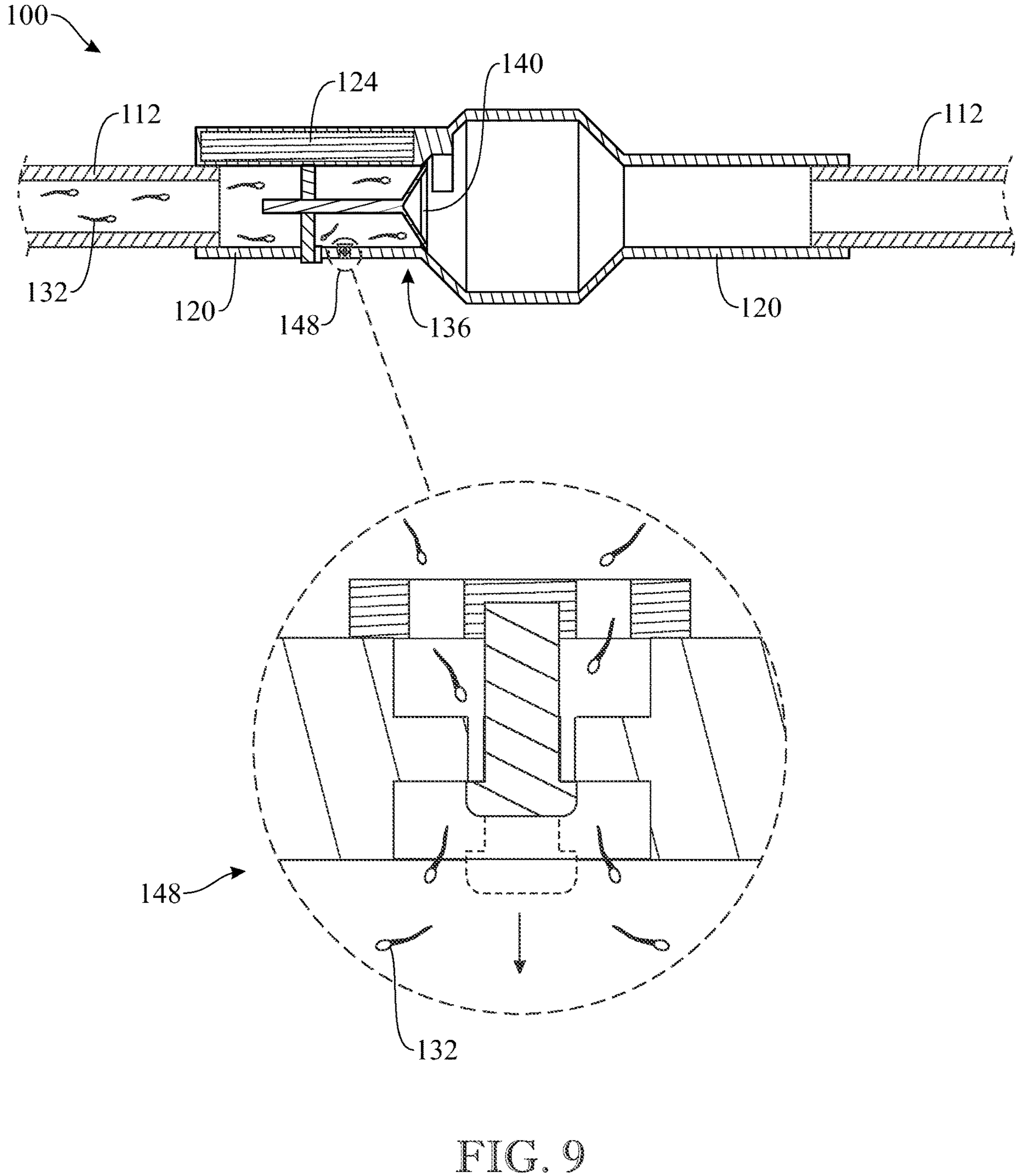
FIG. 9 shows the side, longitudinal cross-sectional view of the reversible male contraceptive implant device illustrated in FIG. 7, shown with a blown up outlet allowing for obstructed sperm to flow into the scrotum.

The device may also contain an outlet 148 designed for obstructed sperm 132, as shown in FIG. 9. This outlet 148 may allow for the controlled release of obstructed sperm 132 into the scrotum. By providing an outlet 148 for obstructed sperm, the device ensures that it can be safely eliminated by the body's immune system.

The present invention of the reversible male birth control implant device offers a range of possibilities for alternate embodiments, allowing for customization and adaptation to individual needs. One alternative embodiment entails the utilization of diverse materials for the tubular component, such as biocompatible polymers like medical-grade silicone, expanding the material options to cater to specific preferences. Additionally, the wireless receiver can be designed to be compatible with a variety of wireless signals, accommodating different external controllers and enhancing flexibility for users. Another potential embodiment involves the integration of additional sensors or feedback mechanisms within the device, enabling real-time monitoring and data collection regarding sperm flow and fertility status. This enhancement would provide users with valuable insights into their reproductive health. Furthermore, the switching mechanism can be modified to offer adjustable levels of sperm flow obstruction, granting users greater control and precision. These alternate embodiments empower individuals to personalize their contraceptive experience, tailoring it to their unique requirements and preferences.

In summary, the detailed description highlights the unique features and functionalities of the reversible male birth control implant device. By utilizing wireless technology, biocompatible materials, and precise surgical techniques, this device offers a safe, reliable, and user-friendly alternative for male contraception. The ability to switch between states of allowing and blocking sperm flow wirelessly provides users with a convenient and discreet method of controlling their fertility. Furthermore, the compatibility of the device with medical imaging tools, such as MRI, enhances its versatility and long-term usability. The reversible nature of the device allows individuals to regain fertility if desired, providing flexibility in family planning decisions. Overall, this invention represents a significant advancement in the field of male contraception, empowering individuals with greater control over their reproductive health.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A reversible male contraceptive implant device comprising:

a tubular component configured for surgical insertion into each severed vas deferens, wherein proximal and distal ends of each vas deferens are attachable to respective ends of the tubular component;

a wireless receiver coupled to the tubular component, capable of receiving external wireless signals, and responsive to said signals by alternating the device between a first state that permits the flow of sperm through the tubular component and a second state that impedes the flow of sperm; and a switching assembly within the tubular component, responsive to actuation by the wireless receiver, and operable to transition the tubular component between the first state and the second state.

2. The device of claim 1, wherein the wireless receiver is configured to operate without containing any metals that could interfere with MRI imaging.

3. The device of claim 2, wherein the wireless receiver is configured to receive one or a combination of non-biologically harmful wave signals, including radio frequency, ultrasound, and infrared light.

4. The device of claim 3, wherein the wireless receiver requires two or more specific wireless signals to switch between the first state and the second state, enhancing security and safety.

5. The device of claim 4, wherein the wireless receiver converts the received wireless signals directly into electrical and mechanical energy, eliminating the need for an internal battery.

6. The device of claim 5, wherein the wireless receiver provides feedback to the user, confirming successful transitions between the first and second states, and further wherein the wireless receiver is in electronic communication with a smartphone.

7. The device of claim 4, wherein the wireless receiver is shielded to prevent accidental activation due to environmental signals.

8. The device of claim 1, wherein the switching assembly for switching between the first state and the second state comprises a diaphragm located within a dilated portion of the tubular component.

9. The device of claim 8, wherein the diaphragm is made from silicon or polytetrafluoroethylene.

10. The device of claim 9, wherein the diaphragm is designed to return to an original position of the diaphragm after transitioning between the first and second states.

11. The device of claim 1, wherein the tubular component is constructed from a flexible, resilient, and biocompatible material compatible with medical imaging devices.

12. The device of claim 11, wherein the tubular component is constructed from polytetrafluoroethylene.

13. The device of claim 1, wherein the switching assembly for switching between the first state and the second state comprises an inflatable balloon configured to block a lumen of the tubular component.

14. The device of claim 13, wherein the balloon is deflated to transition the device into the first state to permit the flow of sperm.

15. The device of claim 1, wherein the tubular component includes an outlet for redirecting sperm during the second state, facilitating safe removal of sperm from the tubular component into the scrotum.

16. The device of claim 15, wherein the outlet is designed to prevent any buildup of sperm within the tubular component during the second state.

17. The device of claim 1, wherein the switching assembly for switching between the first state and the second state comprises a ball valve to control the flow of sperm through the tubular component.

18. The device of claim 1, wherein the device is designed to facilitate easy surgical insertion and removal to offer a non-permanent male contraceptive solution.

19. A reversible male birth control device, comprising:

a tubular component configured for surgical insertion into each severed vas deferens, wherein the proximal and distal ends of each vas deferens are attachable to respective ends of the tubular component;

a wireless receiver coupled to the tubular component, said wireless receiver configured to operate without metals incompatible with magnetic resonance imaging (MRI) imaging and capable of receiving external wireless signals, said signals requiring two or more specific wireless inputs to switch the device between a first state that permits the flow of sperm through the tubular component and a second state that impedes the flow of sperm;

a switching assembly for switching between the first state and the second state, wherein the mechanism comprises:

a semi-flexible diaphragm positioned within a dilated portion of the tubular component, said diaphragm being made of a biocompatible material selected from the group consisting of silicon and polytetrafluoroethylene; and an outlet configured to redirect sperm from the tubular component into the scrotum during the second state, allowing sperm to be safely absorbed by the body's immune system; wherein the wireless receiver is configured to convert the received wireless signals into electrical and mechanical energy, thereby actuating the switching mechanism without requiring an internal battery; and further wherein the tubular component is constructed from polytetrafluoroethylene, ensuring compatibility with medical imaging devices and enhancing the biocompatibility of the device.

20. A method of providing reversible male contraception, comprising:

surgically implanting a device with a tubular structure in each severed vas deferens such that the proximal and distal ends of each vas deferens are attached to the respective ends of the tubular structure of the device;

operating a wireless receiver attached to the device to receive external wireless signals, which, in response, switches the device between a first state that permits the flow of sperm through the tubular structure and a second state that inhibits the flow of sperm;

managing the exit of sperm from the tubular structure into the scrotum through an outlet within the device when the device is in the second state; and employing a switching assembly within the device, which is actuated by the wireless receiver upon receiving the signals, to facilitate a direct transition between the first and second states.

* * * * *